United States Patent [19]
Robinson et al.

[11] Patent Number: 4,914,245
[45] Date of Patent: Apr. 3, 1990

[54] CULPIN

[75] Inventors: Gordon W. Robinson, Lawrenceville; Joseph O'Sullivan, Belle Mead; Edward Meyers, East Brunswick; Jerry S. Wells, Ringoes; Janice H. Del Mar, Hopewell, all of N.J.

[73] Assignee: E. R. Squibb & Sons, Inc., Princeton, N.J.

[21] Appl. No.: 333,496

[22] Filed: Apr. 5, 1989

[51] Int. Cl.$^4$ .............................................. C07C 39/08
[52] U.S. Cl. ...................................... 568/766; 568/763
[58] Field of Search ................................ 568/763, 766

[56] References Cited
U.S. PATENT DOCUMENTS

| | | | |
|---|---|---|---|
| 2,459,835 | 1/1949 | Monroe | 568/766 |
| 2,801,980 | 8/1957 | Spacht | 568/766 |
| 2,801,981 | 8/1957 | Spacht | 568/766 |
| 4,590,304 | 5/1986 | Wallace | 568/766 |

FOREIGN PATENT DOCUMENTS 0141732 11/1979 Japan .................................... 568/766

OTHER PUBLICATIONS

R. F. Cain, "Studies of Caprophilous Ascomycetes", Can. J. Botany, vol. 39; 1633–1666 (1961).
R. E. Schwartz et al., "L-657,398, A Novel Antifungal Agent: Fermentation, Isolation, Structural Elucidation and Biological Properties", J. of Antiobiol., vol. XLI, No. 12, p. 1774–1779 (Dec. 1988).

Primary Examiner—Werren B. Lone
Attorney, Agent, or Firm—Theodore R. Furman, Jr.

[57] ABSTRACT

Cultivation of a strain of the microorganism, Preussia sp., that has been deposited in the American Type Culture Collection as A.T.C.C. No. 20,923, yields a novel antibiotic substance, culpin, that has activity against a selected spectrum of microorganisms.

3 Claims, 5 Drawing Sheets

CULPIN

SUMMARY OF THE INVENTION

Cultivation of a strain of the microorganisms, Preussia sp., that has been deposited in the American-Type Culture Collection as A.T.C.C. No. 20,923, yields a novel antibiotic substance, culpin, that has activity against a selected spectrum of microorganisms. Culpin, 2-(3-methyl-2-butenyl)-5-(3-methyl-3-buten-1-ynyl)-1,4-benzenediol, has the structure

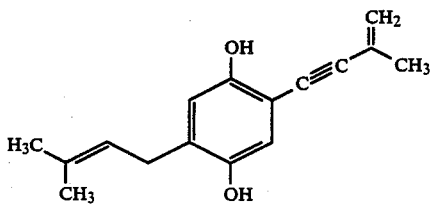

DETAILED DESCRIPTION OF THE INVENTION

The Microorganism

Figure 1:
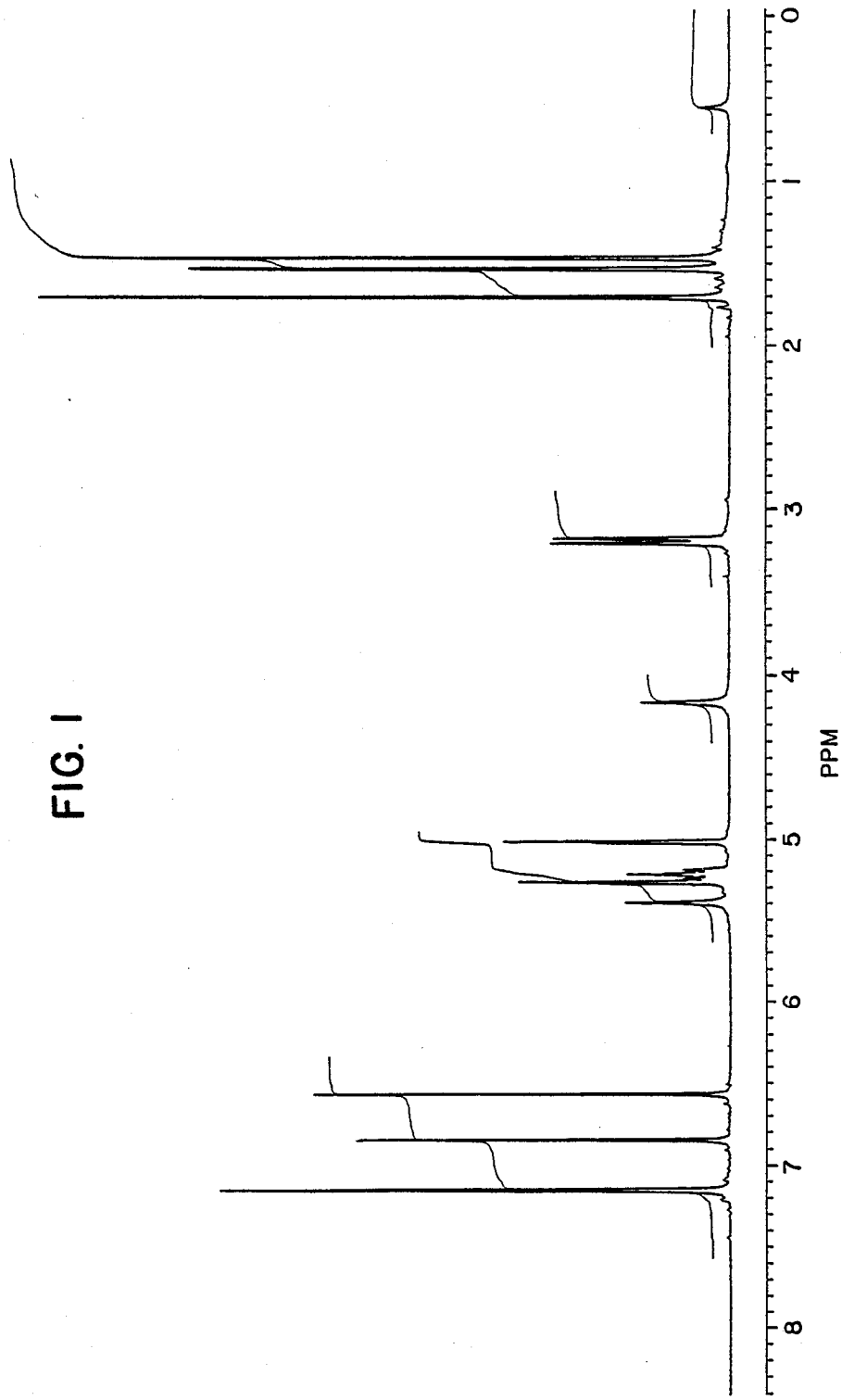
FIG. 1 is the 270 MHz proton NMR ($C_6D_6$) spectrum of culpin.

The microorganism used for the production of culpin is a strain of Preussia, isolated from a soil sample obtained in Culpepr, Virginia. Isolation of the organism from the soil sample was accomplished by placing about 0.5 to 1.0 g of soil in a tube with 10 ml of a sterile solution containing 0.1 percent gelatin and salts. After vigorous shaking, a small aliquot was placed onto the surface of a nutrient agar in a Petri dish. The agar had the following composition:

| | |
|---|---|
| Beef extract | 3.0 g |
| Polypeptone peptone | 5.0 g |
| Lactose | 10.0 g |
| Agar | 10.0 g |
| Distilled water to 1000 ml | |
| Bromcresol purple | 2.5 ml of a 1 mg/ml solution |
| Penicillin | 10.0 ml of a 0.16% solution |
| Chloramphenicol | 8.0 ml of a 0.25% solution |
| Streptomycin sulfate | 1.0 ml of a 1.5% solution |

The bromcresol purple, penicillin, choramphenicol and streptomycin sulfate solutions were filter sterilized before being added to the basal medium that had been sterilized by autoclaving at 121° C. for 20 minutes.

After inoculation, the plates were incubated for 4 days at 25° C. At that time, the colonies of Preussia sp. were picked and transferred to Potato-Dextrose Agar (Difco) medium for maintenance. A subculture of the organism can be obtained from the American-Type Culture Collection, Rockville, Md. Its accession number in this repository is A.T.C.C. No. 20,923. In addition to the specific organism described and characterized herein, it should be understood that mutants of the microorganism produced through the use of chemical or physical mutagens can also be cultivated to produce the subject compound.

The following characteristics serve to identify the culture as a species of Preussia. When grown on potato-dextrose agar or tomato juice agar, the culture readily produces sexual fruiting bodies bearing asci and ascospores. The organism is a saprophyte and a coprophilous Ascomycete.

Histological examination of thin sections shows the fruiting body to be a cavity within stromatic tissue. The asci are arranged in parallel fascicles arising from the base of the cavity. Paraphyses (long filiform cells) are interspersed between the asci. The asci are $61\mu \times 16\mu$, 8-spored, broadly clavate, stipitate (with a basal stem) attached to a crozier, the site where meiotic division occurs. There is no pore at the apex of the ascus or any other means of dehiscence. At matuity, the ascus wall becomes evanescent, and the spores are liberated. The ascospores are $8.2\mu \times 5.4\mu$, dark brown, opaque, thick-walled, and have an elongated germinal slit extending the full length of each cell. Some spores with transverse septa divide mitotically, doubling the number of ascospores per ascus. At maturity, ascospores within an ascus may number as many as 32.

The characteristics are in agreement with the generic description of Preussia given by Cain, R. F. in his article, "Studies of Coprophilous Ascomycetes, VII, Preussia, *Can. J. Bot.*, 39:1633-1666 (1961).

Production of the Antibiotic

Preussia sp., A.T.C.C. No. 20,923, produced culpin possessing activity against microorganisms. To form the antiobiotic according to the preferred fermentation method, Preussia sp., A.T.C.C. No. 20,923, was grown at or near room temperature (25° C.) under submerged, aerobic conditions in an aqueous nutrient medium containing an assimilable carbohydrate and nitrogen source. The fermentation was carried out until substantial activity was imparted to the medium, usually about 96–120 hours.

After completion of the fermentation, the mycelia were separated from the harvested broth by centrifugation. The mycelial cake was extracted with methanol and the extract was concentrated in vacuo to remove the organic solvent, leaving an aqueous suspension. After acidification of this aqueous layer to pH about 4, the acitivy was extracted into ethyl acetate. The ethyl acetate extract was then concentrated to dryness in vacuo, and the resulting residue, dissolved in chloroform: methanol, 98:2 (v/v), was purified by column chromatography on silica gel. The developing solvent was the same as that used to dissolve the residue. Monitoring of the eluates was dones by thin layer chromatography on silica gel with chloroform:ethyl acetate, 3:7 v/v, as the developing solvent, with detection of the components by bioautography on Saccharomyces cerevisiae or by iodine vapor visualization. Fractions containing culpin were pooled and concentrated to dryness in vacuo. Further purification was effected by repeating the silica gel chromatography. The active fractions were again pooled and concentrated in vacuo to give an off-white solid. Final purity was achieved by recrystallization from benzene-heptane. Culpin was also recovered from the broth supernatant by extraction with ethyl acetate after acidification of the filtrate to a pH about 4. Purification of culpin was then carried out in the same manner as described for purification from the mycelial cake.

Culpin can be used to combat bacterial infections in mammalian species, such as domesticated animals (e.g., dogs, cats, cows, horses and the like) and humans. They can be administered using modes of administration which have been used in the past to deliver penicillins and cephalosporins to the site of the infection. Such methods of administration inlcude intravenous and intramuscular infections and as a suppository. For a human adult, daily dose of about 250 milligrams to about 2 grams are exemplary. Additionally, culpin is useful as a disinfectant and for suppressing the growth of susceptible microorganisms, e.g. on surgical instruments. Further information about the potency of the compound of this invention is set forth below under the heading "Biological Activity".

The following examples further illustrate the preparation and utility of culpin.

EXAMPLE 1

Fermentation of Preussia sp., A.T.C.C. No. 20,923

Preussia sp., A.T.C.C. No. 20,923, was maintained on Potato-Dextrose Agar (Difco). These slants served as the source of inoculum for 100 ml of medium contained in 500 ml of Erlenmeyer flasks. The medium had the following composition:

| | |
|---|---|
| Toasted nutrisoy flour | 15.0 g |
| Soluble starch | 15.0 g |
| Glucose | 50.0 g |
| $CoCl_2 \cdot 6H_2O$ | 0.005 g |
| $CaCO_3$ | 10.0 g |
| Distilled water | to 1000 ml |

The medium was sterilized by autoclaving at 121° C. for 30 minutes.

After incoluation, the flasks were inoculated on a rotary shaker (300 rpm, 2-inch throw) at 25° C. for 120 hours. After the incubation period, 5% (v/v) transfers were made from the grown culture flasks to twenty, 500 ml Erlenmeyer flasks each containing 100 ml of the following medium:

| | |
|---|---|
| Malt extract | 10.0 g |
| Yeast extract | 10.0 g |
| Peptone | 1.0 g |
| Dextrose | 20.0 g |
| Distilled water | to 1000 ml |

The medium was adjusted to pH 7 before sterilization at 121° C. for 20 minutes.

The flasks were again incubated at 25° C. on a rotary shaker (300 rpm, 2-inch throw) for 120 hours, at which time the contents of the flasks were pooled.

EXAMPLE 2

Isolation of Culpin

The pooled broth was centrifuged to pellet the mycelium. The supernatant was worked up separately. The mycelium (360 g wet weight) was suspended in 1 liter of methanol and the whole stirred at room temperature for about one hour. The methanolic extract was freed from the mycelium by filtration and concentrated in vacuo to approximatley 100 ml. The pH of the concentrate was adjusted to pH 4.5 with 1N HCl. The acidified solution was then extracted twice with 150 ml portions of ethyl acetate. The ethyl acetate layers were combined, washed once with water (50 ml), dried over $MgSO_4$ and concentrated in vacuo to yield 2.8 g of brown oil. The oil was dissolved in 10 ml of a solvent consisting of $CHCl_3$: MeOH, 98:2, v/v, and filtered through 40 ml of silica gel. The activity was washed through with 175 ml of the same solvent and the filtrate concentrated in vacuo to give 0.78 g of brown oil. The oil was charged onto a silica gel column (Merck silica gel), 2.5×21 cm, packed in $CHCl_3$:MeOH, 98:2, v/v, and the column was eluted with the same solvent, at a flow rate of 2 ml/minute. Fractions of 2.8 ml were collected for the first 45 tubes, after which fractions of 4.0 ml were collected. Each fraction was tested for bioactivity by a conventional paper-disc, agar diffusion assay v. Saccharomyces cerevisiae. Active fractions were also monitored by thin layer chromatography on silica gel (Merck) with $CHCl_3$:EtOAc, 3:7, v/v, as the developing solvent. Visualization was by bioautography v. Saccharomyces cerevisiae or by exposure to iodine vapor. Active fractions containing culpin were combined and the pool concentrated in vacuo to yield 131.4 mg of a yellow solid. Further purification of this material was effected by chromatography on a silica gel (Merck) column (1.5×22 cm) with $CHCl_3$:MeOH; 98:2, v/v. The column was packed in this same solvent. The pooled active fractions were concentrated in vacuo to give 92.8 mg of culpin as an off-white solid that was crystallized from benzene-heptane (m.p. 98–100° C.).

Characteristics of Culpin

Culpin is an off-white, neutral substance, $^1H$ NMR (270 MHz, $C_6D_6$):$\delta$6.85 (s, 1H), 6.57 (s, 1H), 5.39(br s, 1H, —OH), 5.27(m, 1H), 5.22(m, 1H), 5.02(m, 1H), 4.17(br s, 1H, —OH), 3.19(d, 2H), 1.71(t, 3H), 1.54(br s, 3H), 1.47(br s, 3H). (See FIG. 1).

Figure 2:
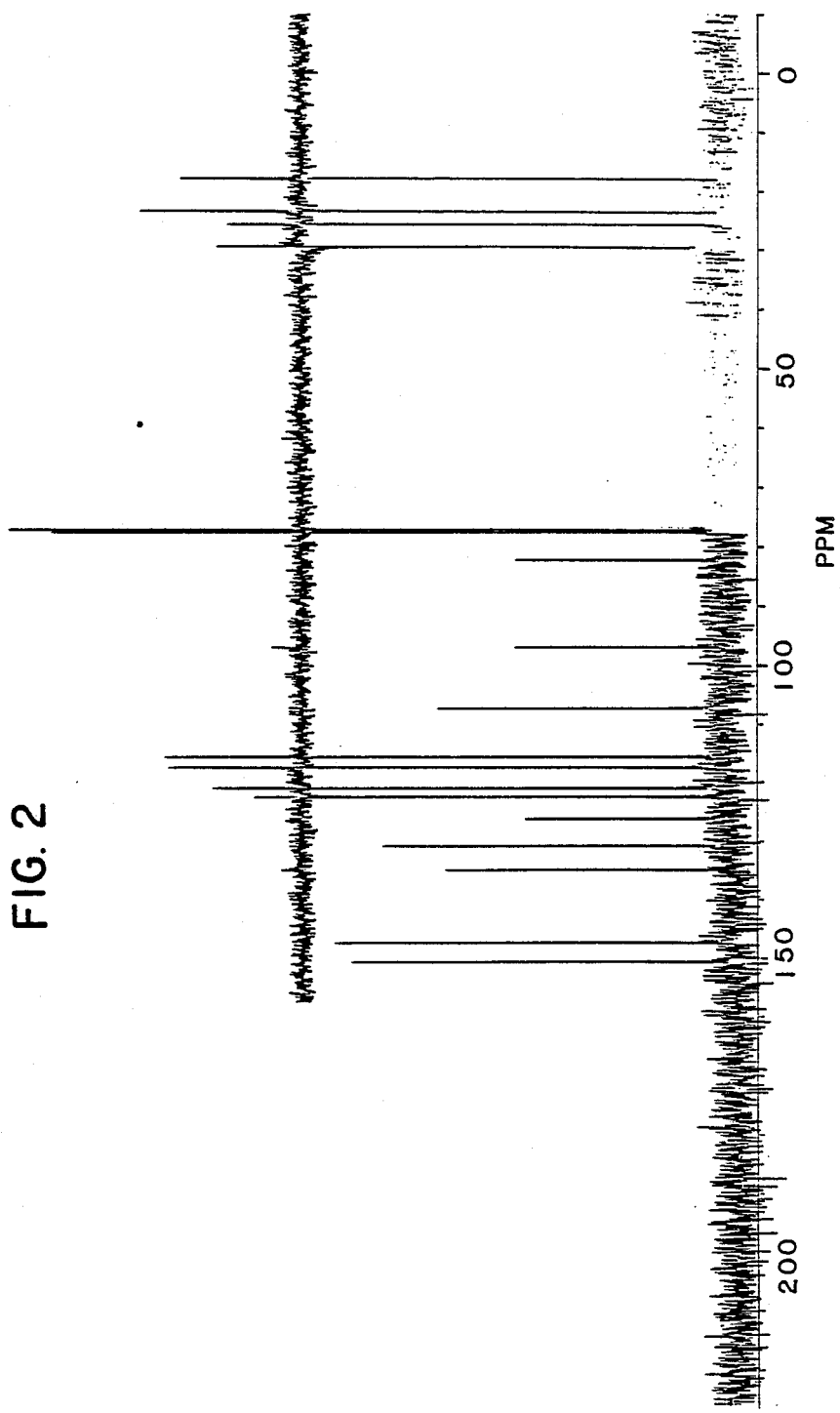
FIG. 2 is the 67.5 MHz carbon-13 NMR ($CDCl_3$) spectrum of culpin.

$^{13}C$ NMR (67.5 MHz, $CDCl_3$): $\delta$150.5, 147.3, 134.9, 130.8, 126.2, 122.5($CH_2$), 121.0(CH), 117.5(CH), 115.6(CH), 107.3, 97.0, 82.1, 29.5($CH_2$), 25.7($CH_3$), 23.4($CH_3$), 17.8($CH_3$). (See FIG. 2).

Figure 3:
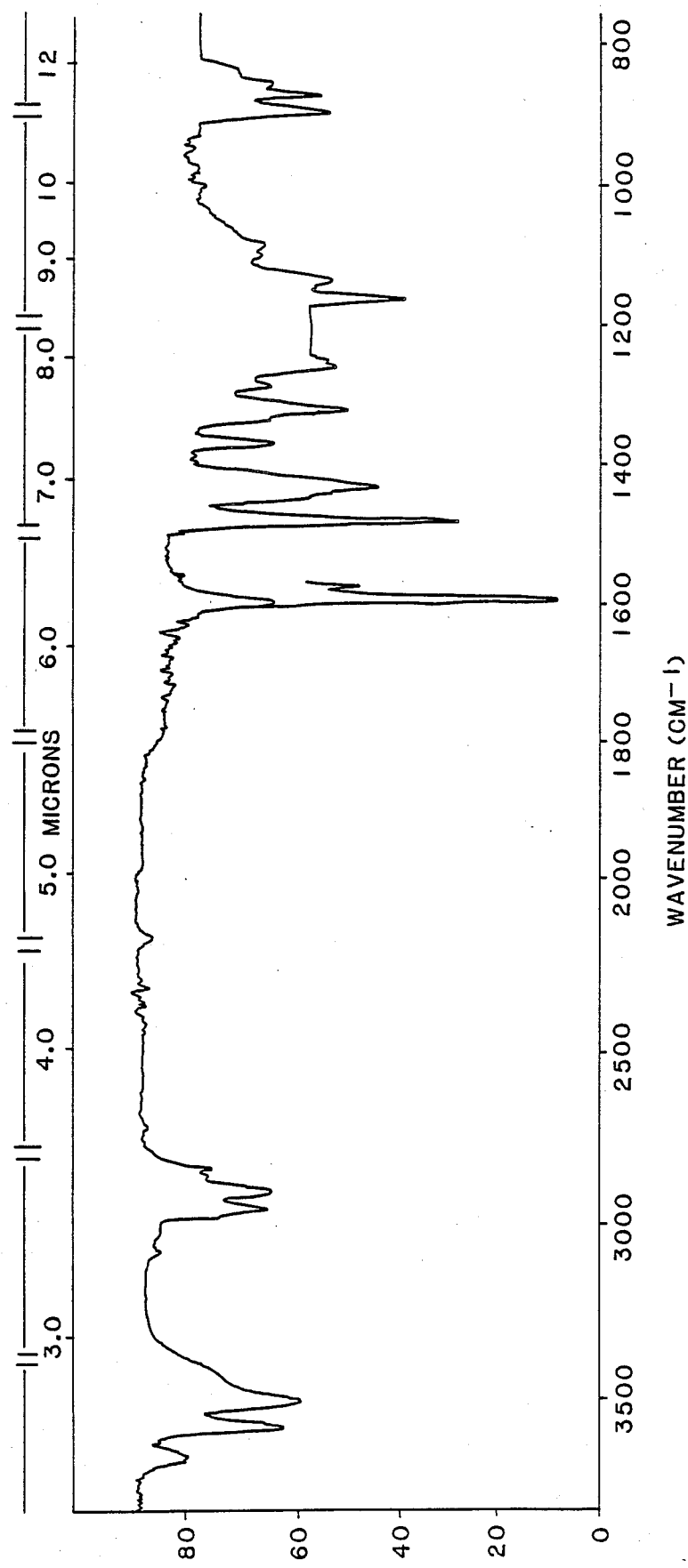
FIG. 3 is the infrared spectrum of culpin in $CHl_3$.

IR ($CHCl_3$) $cm^{-1}$: 3590, 3515, 2960, 2905, 2180(weak), 1600, 1485, 1435, 1370, 1320, 1165, 900, 875. (See FIG. 3).

Figure 4:
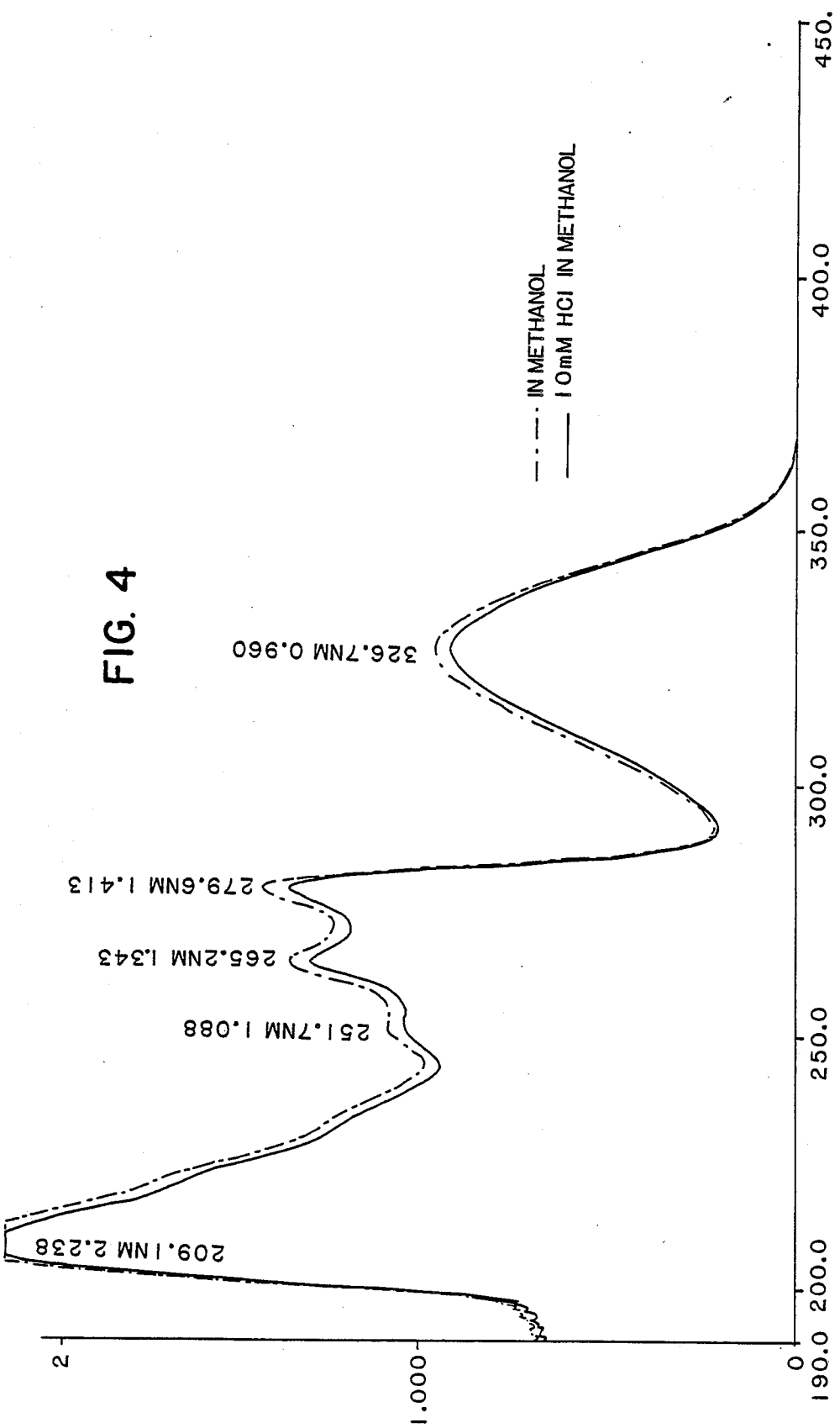
FIG. 4 is the ultraviolet spectrum of culpin (in methanol and methanol with 0.01 N HCl).

UVC$\lambda$max($\epsilon$):In MeOH and MeOH with 0.01 N HCl: 210(30,000), 252(13,400), 265(16,500), 280(17,400) 326nm(11,800). (See FIG. 4)

Figure 5:
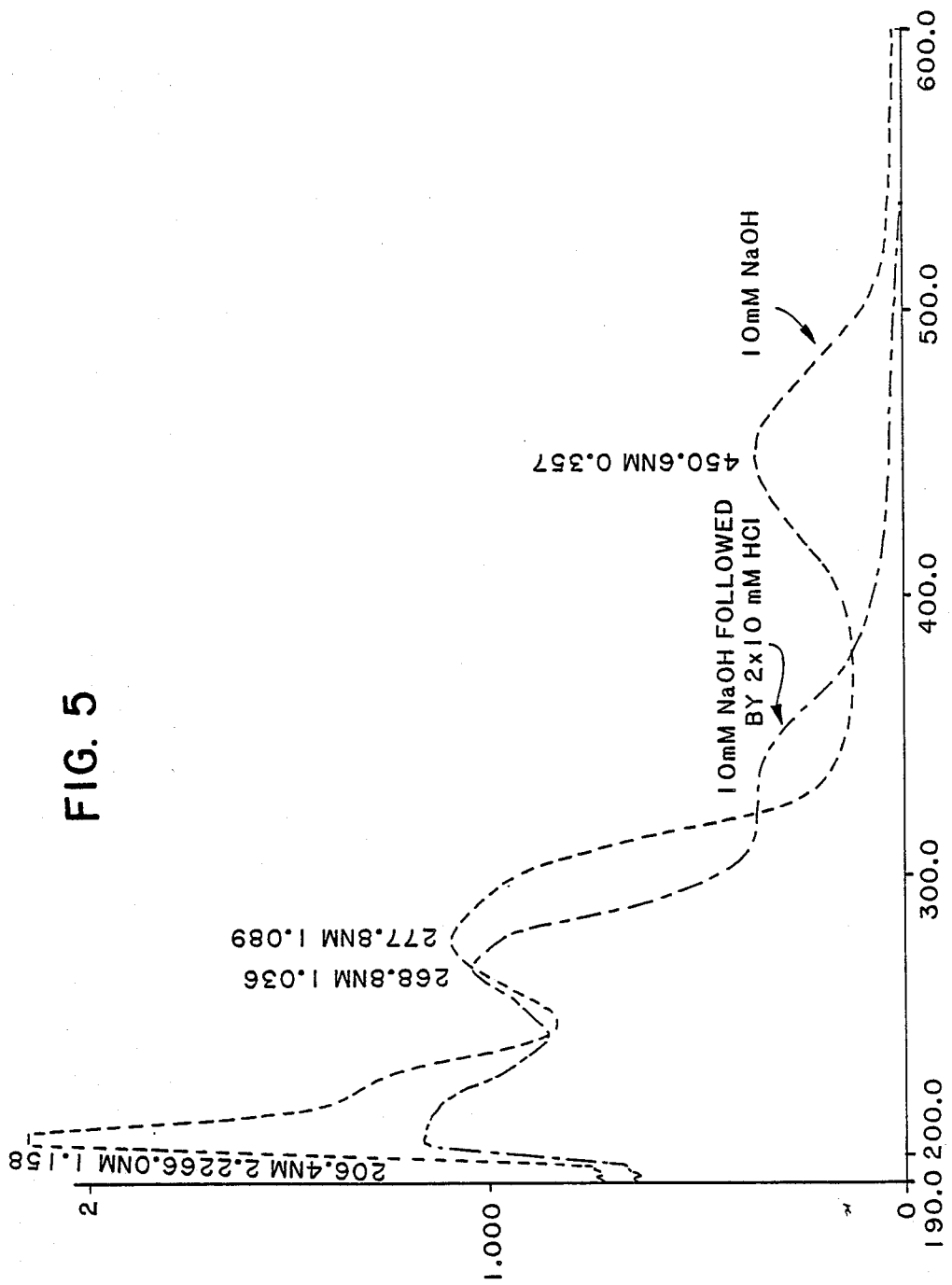
FIG. 5 is the ultraviolet spectrum of culpin (in methanol with 0.01 N NaOH).

In MeOH with 0.01 N NaOH (206(30,000), 278(13,200), 451nm(4,300). (See FIG. 5).

C, H and N Calculated: C, 79,31; H, 7.49; O, 13.20; Found: C, 78,94, H, 7.79; O, 13.27.

Biological Activity

The following methodology was used to determine the minimum inhibitory concentration (hereinafter referred to as MIC) of the compounds of this invention against bacteria. The test organisms were grown in 20 ml of Antibiotic Assay Broth (Difco) by inoculating the broth (in tubes) with a loopful of the organism from a BHI (Difco) agar slant. The inoculated tubes were incubated at 37° C. for 18 to 24 hours. These cultures were assumed to contain $10^9$ colony forming units (CFU) per ml. The cultures were diluted 1:100 to give a final inoculum level of $10^7$ CFU; dilutions were made with Yeast Beef Broth (Difco). The test compounds were dissolved in an appropriate diluent at a concentration of 1,000 $\mu$g/ml. Two-fold dilutions were made in Yeast Beef Broth (Difco), resulting in a range from 1000 $\mu$g/ml to 0.5 μg/ml. A 1.5 ml portion of each dilution was placed into individual petri dishes to which 13.5 ml of K-10 agar was added. The composition of K-10 agar is

| Beef extract | 1.5 g |
|---|---|
| Yeast extract | 3.0 g |
| Peptone | 6.0 g |
| Dextrose | 1.0 g |
| Agar | 15.0 g |
| Distilled water | q.s. to 1000 ml |

The final drug concentration in the agar ranged from 100 μg/ml to 0.05 μg/ml. Organism growth control plates containing agar only were prepared and inoculated before and after the test plates. The organisms were applied to the agar surface of each plate with a Denly Multipoint Inoculator (which delivers approximately 0.001 ml of each inoculum) resulting in a final inoculum of $10^4$ CFU on the agar surface.

The plates were incubated at 37° C. for 18 hours and the MICs determined. The MIC is the lowest concentration of compound inhibiting growth of the organism.

The methodology described above was modified in the assay for activity vs. yeasts and fungi. Fresh F-4 slants of the test organisms were obtained from frozen vials (−70° C.). All cultures were inoculated at 37° C. for 18 to 24 hours, at which time the average cell count was assumed to be 5 x $10^7$ CFU per ml. These were diluted to 1:50 with fresh F-4 broth to give an inoculum level of 1×$10^6$ CFU per ml. The organisms were then dispersed into a sterile template (0.8 ml per well) and delivered onto the agar surface of each plate with a Denly Multipoint Inoculator, resulting in a final inoculum of $10^3$ CFU on the agar surface. The composition of the F-4 broth is:

| Tryptone | 5 g |
|---|---|
| Malt extract | 3 g |
| Glucose | 10 g |
| Yeast extract | 3 g |
| Distilled water | q.s. to 1000 ml |

The medium was sterilized at 121° C. for 15 minutes at 15 psi.

F-4 agar has the same composition as the broth but with the addition of 15 g agar per liter.

The results of the agar dilution assays of culpin were:

| Organism | S.C. No.* | MIC (μg/ml) |
|---|---|---|
| Streptococcus agalactiae | 9287 | 50 |
| Micrococcus luteus | 2495 | 100 |
| Escherichia coli | 10909 | 100 |
| Mycobacterium fortuitum | 8571 | 50 |
| Candida tropicalis | 2963 | 50 |
| Candida tropicalis | 9861 | 50 |

*SC No. is the number in the microorganism collection of E. R. Squibb & Sons, Inc., Princeton, New Jersey.

What is claimed is:

1. A compound having the formula

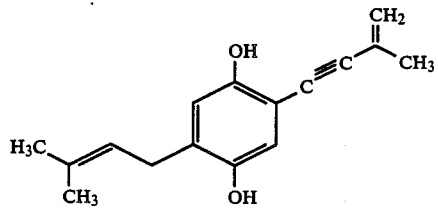

2. A compound of claim 1 having the name 2-(3-methyl-2-butenyl)-5-(3-methyl-3-buten-1-ynyl)-1,4-benzenediol.

3. A compound having the proton NMR spectrum of FIG. 1, the carbon-13 NMR spectrum of FIG. 2, the infrared spectrum of FIG. 3 and the ultraviolet spectrum of FIGS. 4 and 5.

* * * * *